United States Patent [19]

Staniforth

[11] Patent Number: 4,832,880

[45] Date of Patent: May 23, 1989

[54] MANUFACTURE OF MOULDED PRODUCTS

[75] Inventor: John N. Staniforth, Bath, England

[73] Assignee: University of Bath (British Corp.), Bath, England

[21] Appl. No.: 940,021

[22] Filed: Dec. 10, 1986

[30] Foreign Application Priority Data

Dec. 10, 1985 [GB] United Kingdom ............... 85 30365

[51] Int. Cl.[4] ........................ B29C 43/08; A61K 9/20

[52] U.S. Cl. ........................................ 264/22; 264/24; 264/109; 264/113; 264/123; 427/3; 427/26; 427/133; 425/99; 425/174.8 E

[58] Field of Search ................. 264/24, 122, 123, 124, 264/109, 112, 113, 22; 427/3, 2, 27, 26, 25, 12, 133; 425/99, 174.8 E

[56] References Cited

U.S. PATENT DOCUMENTS

| | | | |
|---|---|---|---|
| 3,278,656 | 10/1966 | Dicks et al. | 264/24 |
| 3,478,387 | 11/1969 | Ruekberg | 425/174 |
| 3,626,043 | 12/1971 | Flipot et al. | 264/37 |
| 3,930,061 | 12/1975 | Scharfenberger | 427/27 |
| 3,957,662 | 5/1976 | Sangekar et al. | 252/11 |
| 3,995,979 | 12/1976 | Fedrigo | 425/78 |
| 4,047,866 | 9/1977 | Shah | 425/107 |
| 4,323,530 | 4/1982 | Voss et al. | 264/109 |
| 4,359,192 | 11/1982 | Takahashi et al. | 427/27 X |

FOREIGN PATENT DOCUMENTS

| | | | |
|---|---|---|---|
| 1340494 | 12/1973 | United Kingdom . | |
| 2053787 | 2/1981 | United Kingdom | 264/123 |

*Primary Examiner*—Jan H. Silbaugh
*Assistant Examiner*—Mary Lynn Fertig
*Attorney, Agent, or Firm*—Merchant, Gould, Smith, Edell, Welter & Schmidt

[57] ABSTRACT

In a process for the manufacture of a moulded product by compression of a powder or granules in a die, a powdered die lubricant is used, lubricant particles are electrically charged and the charged particles are fed to the die in advance of the moulding powder. An apparatus for carrying out the process is also provided, the apparatus including a first feed for feeding a powdered lubricant to the die, a second feed for feeding moulded powder to the die after the powdered lubricant, and means for maintaining the electrical potential of the die at a predetermined value different from that of the powdered lubricant.

6 Claims, 6 Drawing Sheets

MANUFACTURE OF MOULDED PRODUCTS

Figure 1:
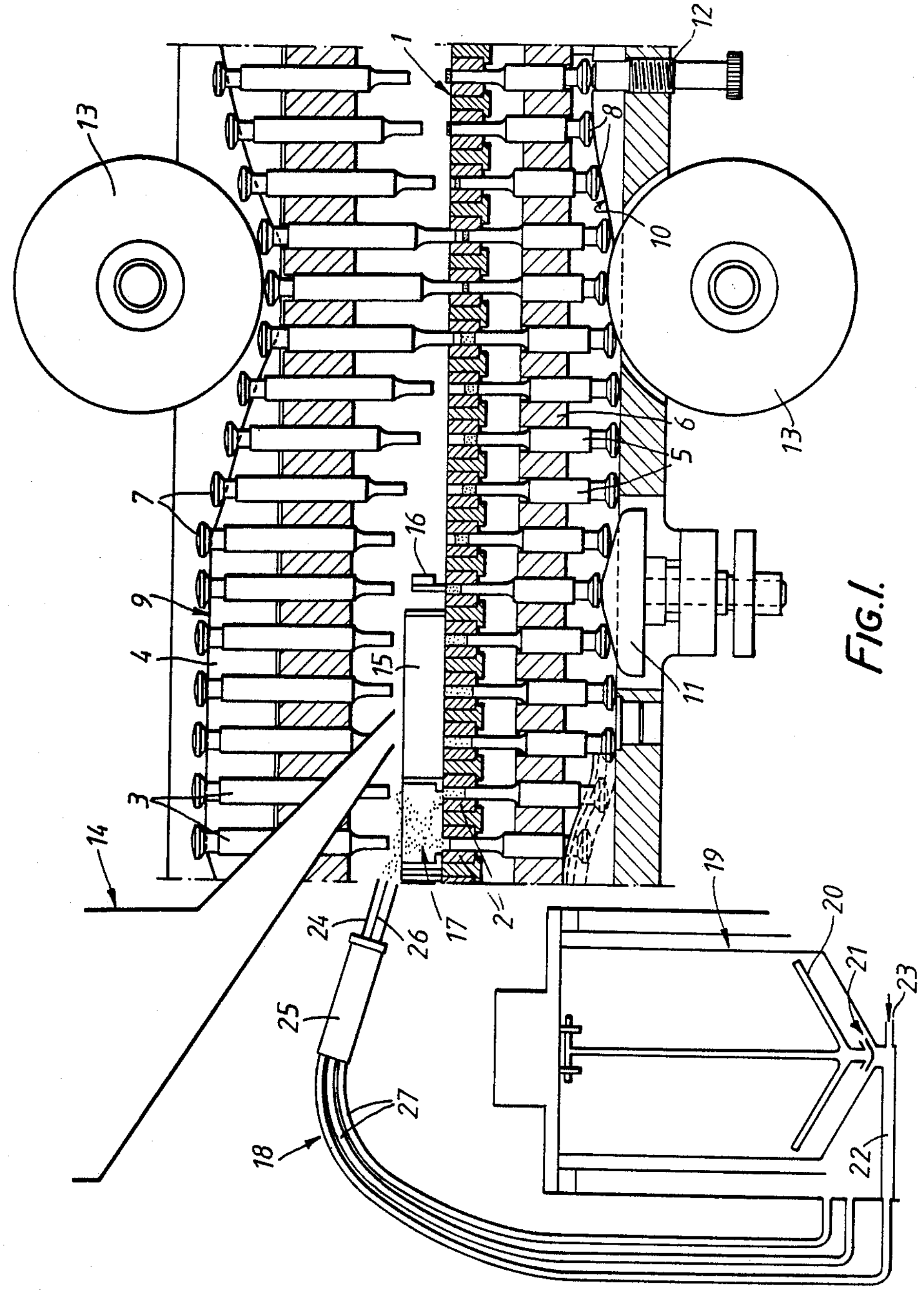

This invention is concerned with moulded products, especially tablets, produced by the compression of powders and granules.

Pharmaceutical tablets are usually prepared by the instantaneous compression of a powder, comprising the active ingredient and an excipient, between two punches in a die. The force for compression may be supplied by either the upper punch or by both the upper and lower punches, but in neither case does all of the applied force go into compressing the powder. Although some of the force is lost in heat and sound energy a major proportion is absorbed in overcoming die wall friction. These frictional forces are sometimes sufficiently great as to prevent tablet compression altogether, and in other cases the appearance of the tablets is unacceptable; for example the tables may be chipped, capped or laminated rendering them unsuitable for further process.

In order to obviate these problems it has been usual to incorporate a lubricant, especially magnesium stearate, in the powder or granules to be tabletted or moulded, normally in a proportion of from 0.25% to 1% by weight. Magnesium stearate has been found to be one of the most efficient tablet lubricants and it also acts as an anti-adherent, preventing powder from sticking to punch faces and die walls. Other lubricant powders, may, however be used as, for example, salts of benzoic acid and polyethylene glycols.

The use of magnesium stearate lubricant has, however, given rise to a number of problems, especially in the production of pharmaceutical tablets but also for other moulded products. The principal problems are as follows:

(a) it is an extremely hydrophobic powder which can adversely affect the bioavailability of drugs and is undesirable in soluble tablets where it produces a surface film or scum on the glass of water in which the tablet is dissolved.

(b) the mixing time used to incorporate the magnesium stearate in the other ingredients of the tablet formulation is critical and can influence the physicomechanical properties of the tablets produced. For example, slight over-mixing is known to seriously reduce the strength of tablets and can produce capping or lamination which completely disrupts tablets.

(c) in common with other tablet lubricant powders, magnesium stearate is incorporated in the whole of the tablet mixture which results in a lubricant coat being formed around most of the granules or particles. This is inefficient since lubricant is only required at the interface between metal and particle surfaces. It is also undesirable since lubricant - excipient and lubricant - active ingredient contact produces poor bonding and seriously weakens the mechanical strength of the tablets produced.

We have now found that the above problems can be substantially obviated and an improved moulded product, especially a tablet, can be obtained by first imparting an electric charge to the lubricant and feeding the charged lubricant to the die in advance of the powder or granules to be compressed being fed to the die.

Accordingly, the present invention provides an improvement in the process for the manufacture of a moulded product by compression of a powder or granules in a die, and in which a powdered die lubricant is used, wherein the lubricant particles are electrically charged and the charged particles are fed to the die in advance of the moulding powder. In this process the lubricant is applied substantially only where it is required at the interface between the metal and moulding powder.

The lubricant particles may be positively or negatively charged and, while it is envisaged that an electrostatic charge would be imparted temporarily, an electret charge could be implanted.

Advantageously, the moulded product is a pharmaceutical tablet and the lubricant is magnesium stearate, and hereinafter the lubricant will be described with reference to magnesium stearate although it will be appreciated that other substances suitable as die lubricants may be used.

The charging of the magnesium stearate particles may be effected by means of a corona discharge system or some other such charging system. Alternatively it would be possible to charge the particles triboelectrically, for example by feeding them rapidly through a nozzle. Preferably the magnesium stearate particles are charged to a potential in the range of 1 to 200 kV.

The magnesium stearate is conveniently mixed with a part of the excipient or carrier, for example, microcrystalline cellulose, lactose or starch, before it is electrostatically charged and fed to the die. The mixing time of the magnesium stearate with the excipient is not critical and, in fact, overmixing may be advantageous, whereas as mentioned above the mixing time is critical when the magnesium stearate is mixed in with the whole of the moulding or tablet formulation.

In the process of the invention a much lower quantity of magnesium stearate is used, for example, approximately one-hundreth of that employed in the known conventional moulding process. The magnesium stearate may be approximately 0.25 to 1.0% by weight of the mixture with the excipient used in the present process, preferably 0.5% by weight.

A small quantity of surfactant, for example, from 2 to 5% by weight of magnesium lauryl sulphate, may be incorporated in the mixture of magnesium stearate and excipient. This has the particular advantage in the case of water soluble or effervescent pharmaceutical tablets that completely clear solutions free from scum are obtained. A glidant may also be added to the magnesium stearate-excipient mixture but will more usually be incorporated in the main moulding powder containing, in the case of pharmaceutical tablets, the active ingredient.

In the process of the invention the magnesium stearate and excipient powder mixture may be filled into a hopper of a dry powder electrostatic charging unit. As will be described in more detail below with reference to the accompanying drawings a spray nozzle from the charging unit may be positioned so as to direct a fine spray of electrostatically charged particles into the front section of a specially constructed feed device for the dies of a rotary press. The charged particles are attracted to the earthed metal surfaces closest to it which include the upper and lower table punch faces and the exposed die wall. The feed rate of the lubricant powder (magnesium stearate and excipient) and charging current and voltage may be adjusted to give optimum lubrication of a given formulation.

Although pressing of pharmaceutical tablets is normally carried out on a rotary press, for example, a Manesty B3B, the process of the present invention can also be carried out on a single punch machine.

The process of the present invention enables moulded products, especially pharmaceutical tablets, to be produced which are substantially stronger, for example, twice as strong, than those produced by the known conventional methods, yet have comparable dissolution rates. Thus, for the same crushing strength tablets produced by the process of the invention have faster dissolution rates than conventionally produced tablets. Further, in view of the absence of large quantities of magnesium stearate within the tablet they are likely to have improved bioavailability, especially in the case of low-solubility drugs.

The invention also provides moulded products, especially pharmaceutical tablets, when obtained by the process of the invention and which have a very low content of lubricant.

The present invention also provides an apparatus for manufacturing a moulded product by compression of a powder or granules in a die, the apparatus including a first feed for feeding a powdered lubricant to the die, a second feed for feeding moulding powder to the die after the powdered lubricant, and means for maintaining the electrical potential of the die at a predetermined value different from that of the powdered lubricant.

Conveniently, the electrical potential of the die is maintained at earth potential.

The lubricant particles are electrically charged and, while, as already indicated, it is possible to implant a permanent electret charge into them, it is preferred to impart a temporary electrostatic charge. Thus the apparatus preferably further includes means for imparting an electrostatic charge to the lubricant; the charge imparting means may comprise a corona charging system.

The charge imparting means is preferably incorporated in the first feed. The lubricant particles can thus be charged just before they reach the die.

Figure 1A:
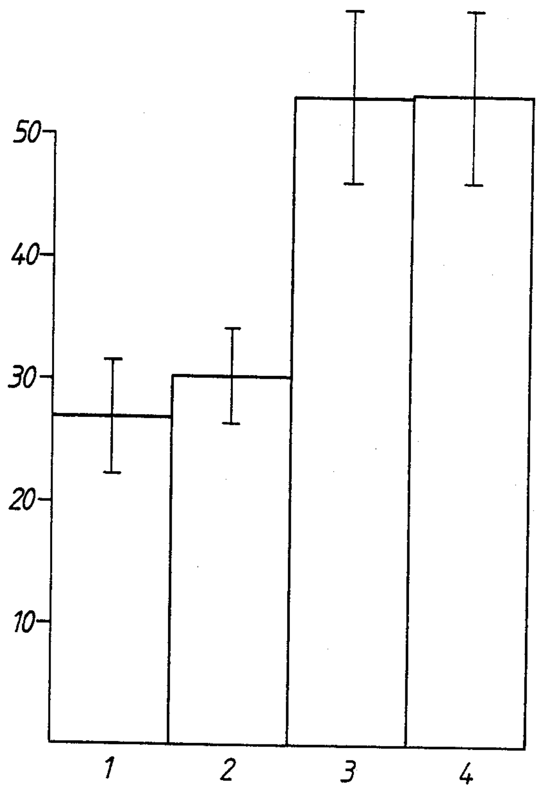
Figure 2:
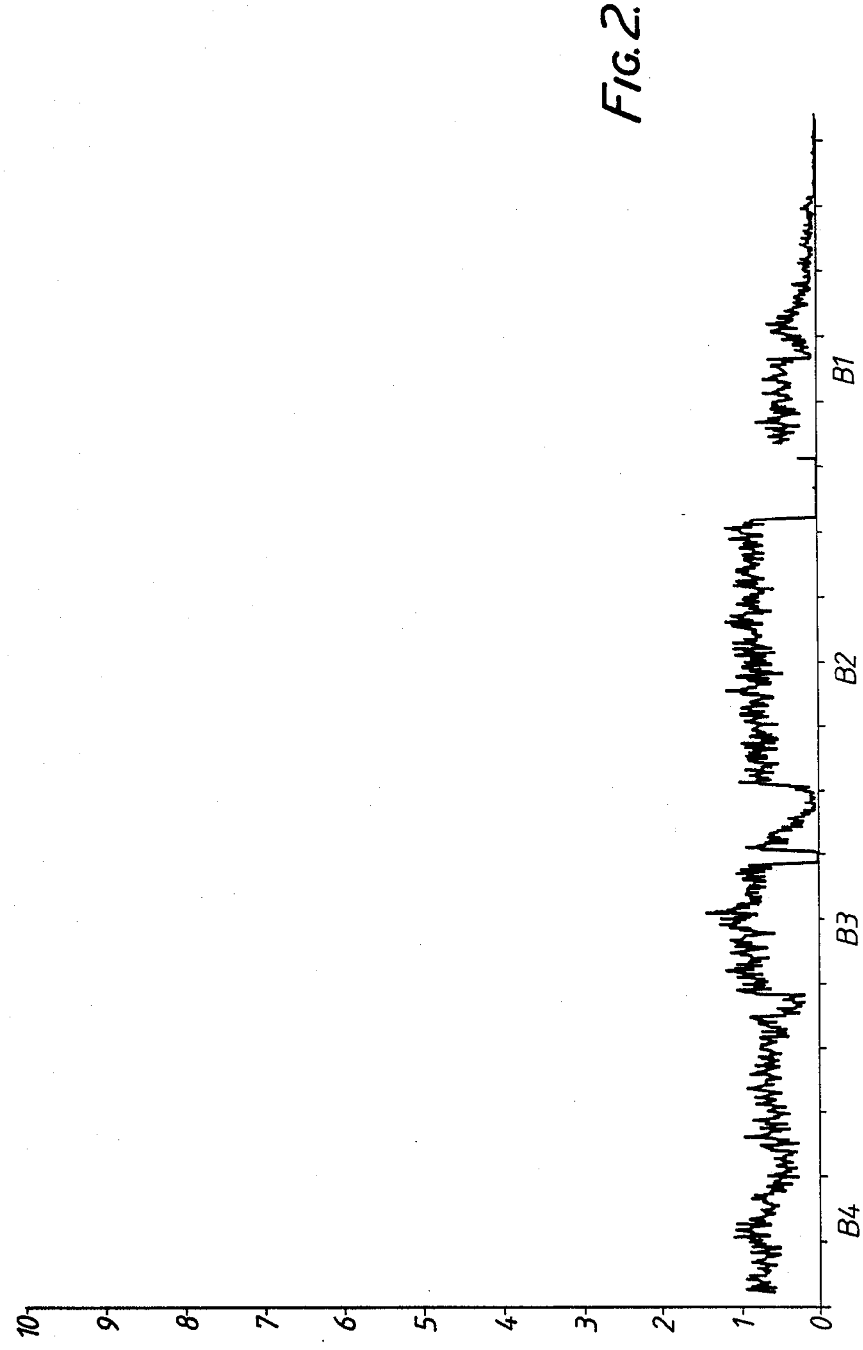
Figure 3:
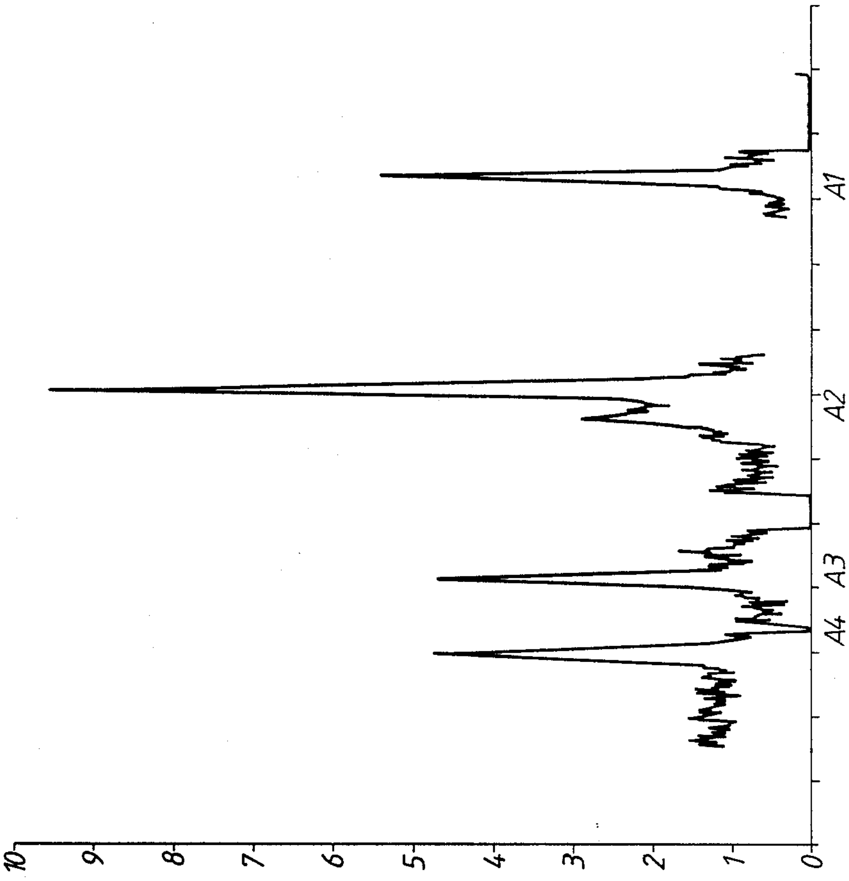
Figure 4:
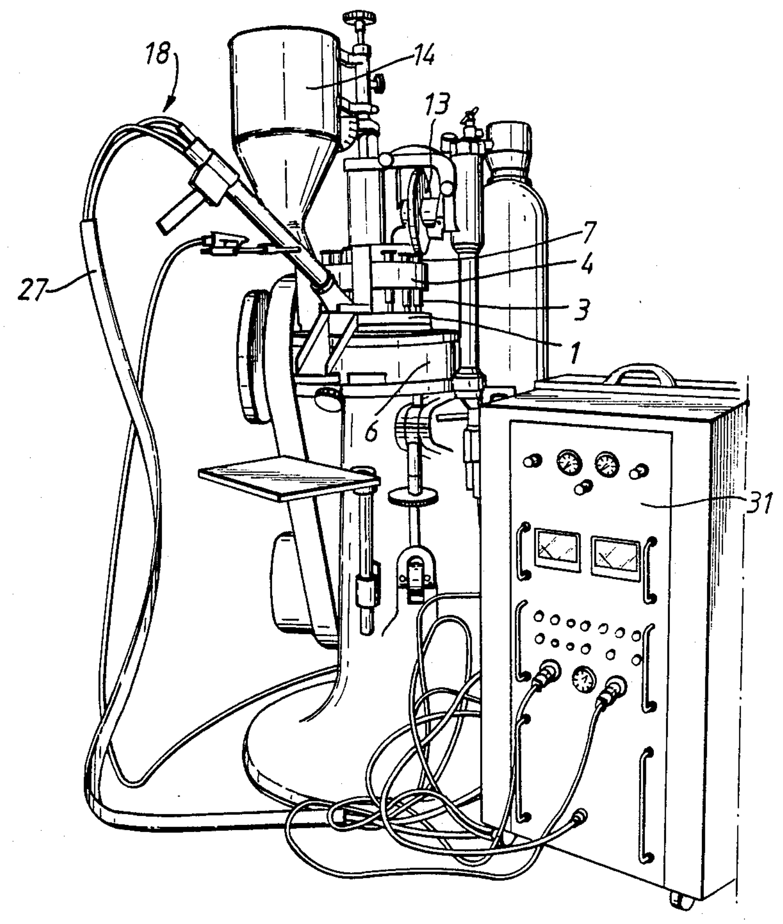
Figure 5:
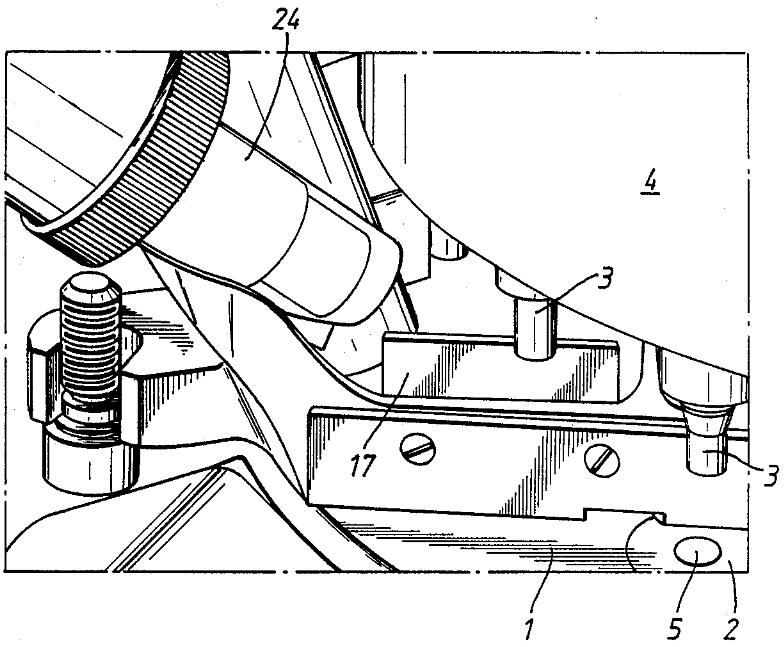

By way of example a rotary press and certain processes embodying the invention will now be described with reference to the accompanying drawings, of which:

FIG. 1 is a schematic developed view of a rotary press,

FIG. 1A is a bar graph comprising strengths of tablets prepared according to the invention with tablets prepared by conventional techniques, FIGS. 2 and 3 are print outs obtained from spectral analysis of tablets prepared by conventional techniques and tablets prepared according to the invention, FIG. 4 is a perspective view of a rotary press embodying the invention that has been used in the laboratory, and FIG. 5 is a perspective view of an electrostatic dry powder spray nozzle mounted on the rotary press.

The rotary press shown in the drawing is in most respects entirely conventional. Thus the press has a circular die table 1 mounted for rotation about its central axis. A plurality of dies 2 are located in the table 1. Above and aligned with each die 2 is an associated upper punch 3 mounted for sliding movement into and away from the die in an upper punch holder 4 which, in turn, is arranged for rotation with the die table 1. Similarly, below and aligned with each die 2 is an associated lower punch 5 mounted for sliding movement into and away from the die in a lower punch holder 6 which, in turn, is arranged for rotation with the die table 1. Each of the upper punches 3 has a cam follower 7 at its upper end and similarly each of the lower punches 5 has a cam follower 8 at its lower end. The cam followers 7 rest on a stationary fixed upper cam track 9 while the cam followers 8 rest on a stationary fixed lower cam track 10. The die table 1, dies 2, punches 3, 5 and punch holders 4, 6 are made of metal.

The lower cam track 10 is interrupted at one position by a ramp 11 the height of which can be screw-adjusted and at another position by the head of an ejection knob 12 which is also screw-adjustable.

A pair of compression rolls 13 are also associated with the upper and lower cam tracks 10 and 11.

The press has a main hopper 14 for feeding the powder or granules to be tabletted. In a conventional arrangement this powder would include lubricant particles but in the described apparatus that is not necessary. The hopper 14 has an outlet leading to a stationary feed frame or a force feeder with moving paddles 15 immediately about the die table 1. The base of the frame 15 lies immediately adjacent to the top of the die table 1 and has apertures which allow powder or granules to pass from the compartment into the dies 2.

A stationary blade 16 is provided for scraping excess powder or granules away from the dies 2.

The apparatus is distinguished from a conventional rotary press by the provision of a supplementary feed frame 17 made partly of insulating material adjacent the frame 15. The supplementary feed frame is supplied with a spray of electrostatically charged lubricant powder from a feed and corona charging device 18 which will now be described.

The device 18 has a powder hopper 19 in which a mixer 20 is provided. The hopper 19 has an outlet 21 to which one end of a conduit 22 is connected; an inlet 23 for compressed air is provided in the conduit 22 adjacent the outlet 21. The other end of the conduit 22 is connected to the corona charging and spraying head 25. The spraying head 25 has an outlet nozzle 24 in the centre of which an electrically conducting spike 26 is provided. The spike 26 is electrically connected to a source of high voltage 31 (not shown in FIG. 1 but shown in FIG. 4) via one or more conduits 27 containing an electrically conducting gel.

The corona charging device described is not in itself a novel device and such a device is sold in the United Kingdom by Volstatic Coatings Ltd..

In operation of the press the die table 1 and the upper and lower punch holders 4, 6, which together form a common unit, are rotated in the direction from left to right as seen in the drawing. It will be appreciated that in the drawing, which is a developed view, the right hand edge of the drawing joins up with the left hand edge.

Lubricant powder in the hopper 19 falls to the outlet 21 of the hopper and is blown from there along the conduit 22 by compressed air entering through the inlet 23. The powder is thus carried to the head 25 and is sprayed out of the nozzle 24 around the spike 26. The spike 26 is maintained at a potential in the range of 1 to 100 kV, preferably 60 kV and as a result the air in the region of the nozzle 24 becomes charged and a charge (which may be positive or negative) is therefore transferred to the powder as it is sprayed.

The die table 1, dies 2, punches 3, 5 and punch holders 4, 6 are all made from electrically conducting material and the whole assembly is maintained at earth potential. Thus, powder sprayed out of the nozzle 24 is attracted to adjacent earthed surfaces and these include the working faces of passing upper and lower punches 3, 5 and exposed parts of passing dies 2. The supplementary feed frame 17, being made of insulating material, does not attract the powder.

After receiving a coating of lubricant powder a given die 2, having an associated lower punch 5 and upper punch 3, moves on to a position underneath the feed frame 15 where the die is filled with powder. As the die moves to that position the cam follower 8 is caused to move down by the downwardly sloping cam track 10 so that the lower punch 5 only just projects into the die and the die is therefore almost entirely filled with powder. The cam follower 8 subsequently reaches the ramp 11 and is driven upwardly thereby expelling powder from the die. While the cam follower 8 is on the top of the ramp 11 the blade 16 scrapes away excess powder from above the die. Thereafter the lower punch 5 is lowered as the cam follower 8 returns to the cam track 10 and the upper punch 3 drops as the cam follower 7 slides down the inclined upper cam track 9. The upper and lower punches 3, 5 are finally forced together by the compression rollers 13 compressing the powder in the die 2 and forming a tablet. Then the upper punch 3 is raised and the lower punch 5 also raised until the tablet is flush with the die table 2 at which stage the tablet is swept away into a collector (not shown) by a wall immediately upstream of the supplementary feed frame 17. The cycle of operation is then repeated.

The position of the nozzle 24 relative to the dies and punches is not critical but a good position can be determined readily by experiment and similarly the best charging conditions can be determined by experiment. Charging has been accomplished successfully with the spike 26 maintained at a potential of 60 kV, the current passing through the spike in this case being 50 $\mu$A. It is believed however that other charging conditions in the range of 1 to 100 kV and 1 to 100 $\mu$A could be satisfactory.

The following Examples illustrate the invention, the parts and percentages being by weight:

Example 1

A tablet moulding powder was prepared by mixing
99 parts of Tablettose with
1 part of salicylic acid:
A lubrication formulation was prepared by mixing
1 part of magnesium stearate with
99 parts of Tablettose.

Tablettose is the trade name of a direct compression lactose.

Tablets were prepared in accordance with the process of the invention by first imparting an electric charge to the lubricant formulation as described above and feeding the charged lubricant formulation to the die of a rotary press in advance of the table moulding powder.

Example 2

A tablet moulding powder was prepared by mixing
99 parts of Tablettose with
1 part of salicylic acid:
A lubrication formulation was prepared by mixing
0.5 parts of magnesium stearate with
99.5 parts of Tablettose.

Tablets were prepared by the method described in Example 1.

The tensile strengths, a measure of the table resistance to mechanical crushing, for the tablets obtained in Examples 1 and 2 is shown in FIG. 1A in comparison with the strengths of tablets produced by conventional methods using the same die wall percentages of magnesium stearate as in Examples 1 and 2.

FIG. 1A is in the form of a bar graph with the bars being referenced 1, 2, 3 and 4. Bars 3 and 4 show the results with tablets produced in accordance with Examples 1 and 2 respectively while bars 1 and 2 show the strengths of tablets produced by conventional methods using the same die wall percentages of magnesium stearate as in Examples 1 and 2. The symbol "I" at the top of each bar graph shows 95 per cent confidence limits about the mean. The "y" axis of the bar graph shows the crushing force in Newtons that the tablet withstood.

Example 1 was also conducted with a lubrication formulation of 5 parts of magnesium stearate to 95 parts of Tablettose and with this formulation the tablet withstood a crushing force of just under 40 N.

Example 3

A tablet moulding powder was made up from
100 parts of Fast flo:
A lubrication formulation was prepared by mixing
1 part of magnesium stearate with
99 parts of Fast flo Tablets were prepared by the method described in Example 1.

Fast flo is the trade name of a direct compression lactose.

Example 4

A moulding powder was made up from
100 parts of Fast flo:
A lubrication formulation was prepared by mixing
0.5 parts of magnesium stearate with
99.5 parts of Fast flo Tablets were prepared by the method described in Example 1.

Example 5

A tablet moulding powder was made up from
100 parts of Fast flo:
A lubrication formulation was prepared by mixing
0.25 parts of magnesium stearate with
99.75 parts of Fast flo Tablets were prepared by the method described in Example 1.

Example 6

A tablet moulding powder was made up from
100 parts of Fast flo:
A lubrication formulation was prepared by mixing
0.5 parts of magnesium stearate,
5.0 parts of magnesium lauryl sulphate and
94.5 parts of Fast flo Tablets were prepared by the method described in Example 1.

They were properly lubricated tablets, the 5.0 per cent magnesium lauryl sulphate being included as a solid surface active agent which is sufficient to solubilise the magnesium stearate when the tablet dissolves. The formulation is therefore suitable for producing tablets which will dissolve in water to give a clear solution. If desired, an effervescent couple (for example, citric acid and sodium bicarbonate) may be incorporated in the moulding powder to give an effervescent solution on dissolving the tablets.

Example 7

A tablet moulding powder was prepared by mixing 50 parts of Avicel PH101 with 50 parts of Microtal A lubrication formulation was prepared by mixing 2 parts of magnesium stearate with 98 parts of Avicel PH101

Tablets were produced by the method described in Example 1.

Avicel is the trade name of a direct compression α-cellulose and Microtal is the trade name of a direct compression sucrose.

Example 8

A tablet moulding powder was made up from 100 parts of Avicel PH101

A lubrication formulation was prepared by mixing 1 part of magnesium stearate with 98 parts of Avicel PH101

Tablets were produced by the method described in Example 1.

The tablets obtained in the above Examples contained only trace quantities of magnesium stearate equivalent to probably less than 5 microgrammes of magnesium stearate in a 500 milligramme tablet. This compares with 5000 microgrammes of magnesium stearate contained in a 500 milligramme tablet at a 1 per cent level produced by a conventional compression moulding method.

FIGS. 2 and 3 illustrate this point. Each figure shows a print out obtained from spectral analysis of the surface of a tablet. FIG. 3 shows the results for four tablets A1 to A4 produced by a conventional lubrication technique and it will be seen that in each case there is a clear peak in the print out indicating the presence of the magnesium stearate. In contrast, FIG. 2 shows the results for four tablets B1 to B4 produced by the process of the invention and in each case there is no clear peak at all in the print out, the amount of magnesium stearate being sufficiently low that the "peak" is lost in the general background noise.

An example of the arrangement of the charging apparatus around the tablet is shown in FIG. 4 of the accompanying drawings in which parts corresponding to those shown in FIG. 1 are referenced by the same reference numerals. The arrangement shown is one that has been used in laboratory tests.

Details of the application of the lubrication formulation to the upper and lower punches and the die walls using a modified electrostatic dry powder spray nozzle 24 is shown in FIG. 5 of the accompanying drawings in which parts corresponding to those shown in FIG. 1 are referenced by the same reference numerals.

I claim:

1. A process for the manufacture of a tablet by compression of a tablet material in the form of a powder or granules in a rotary press, the process comprising the steps of:

rotating a plurality of dies around a central axis of the press, the dies having associated upper and lower punches which rotate with the dies;

electrically charging a lubricant while maintaining the electrical potential of the dies and the punches at a potential different from that of the lubricant;

feeding the lubricant to a fixed region of the press in advance of a filling station from where the lubricant is attracted by virtue of its electrical charge onto each of said upper and lower punches and into each of said dies while they are rotating and as they pass through the region toward the filling station;

filling the dies with tablet material to be compressed while they are rotating around the central axis and as they pass through the filling station;

compressing the tablet material in the dies between working faces of the punches to form tablets; and ejecting the tablets from the dies.

2. A process as claimed in claim 1 wherein the lubricant is magnesium stearate.

3. A process as claimed in claim 1 wherein the charging of the lubricant is effected by means of a corona discharge system.

4. A process as claimed in claim 1 wherein the lubricant is charged tribo-electrically.

5. A process as claimed in claim 1 wherein the lubricant is charged to a potential of 1 to 100 kV.

6. A process as claimed in claim 1 wherein the lubricant is mixed with a part of the excipient used in the moulding formulation.

* * * * *